United States Patent
Drus et al.

(10) Patent No.: US 10,744,474 B2
(45) Date of Patent: Aug. 18, 2020

(54) QUENCHING SYSTEM

(71) Applicant: Borsig GmbH, Berlin (DE)

(72) Inventors: Sebastian Drus, Hoppegarten (DE); Carsten Birk, Glienicke (DE)

(73) Assignee: BORSIG GMBH, Berlin (DE)

( * ) Notice: Subject to any disclaimer, the term of this patent is extended or adjusted under 35 U.S.C. 154(b) by 0 days.

(21) Appl. No.: 16/295,474

(22) Filed: Mar. 7, 2019

(65) Prior Publication Data

US 2019/0275488 A1    Sep. 12, 2019

(30) Foreign Application Priority Data

Mar. 9, 2018 (DE) .................. 10 2018 002 086

(51) Int. Cl.
| | | |
|---|---|---|
| *B01J 8/04* | (2006.01) | |
| *C07C 4/04* | (2006.01) | |
| *C10G 9/00* | (2006.01) | |
| *F28C 3/08* | (2006.01) | |
| *F28D 21/00* | (2006.01) | |

(52) U.S. Cl.
CPC ............. *B01J 8/0496* (2013.01); *C07C 4/04* (2013.01); *C10G 9/002* (2013.01); *F28C 3/08* (2013.01); *B01J 2208/0053* (2013.01); *B01J 2208/00176* (2013.01); *B01J 2208/00283* (2013.01); *B01J 2208/00309* (2013.01); *F28D 2021/0075* (2013.01)

(58) Field of Classification Search
CPC ............. B01J 2219/00087; B01J 2219/00103
See application file for complete search history.

(56) References Cited

U.S. PATENT DOCUMENTS

| | | | |
|---|---|---|---|
| 4,098,324 A | 7/1978 | Kümmel et al. | |
| 4,479,869 A * | 10/1984 | Petterson | ................ C10G 9/36 208/130 |
| 4,614,229 A | 9/1986 | Oldweiler | |
| 2008/0121383 A1 | 5/2008 | Birk | |
| 2008/0289588 A1 * | 11/2008 | Wees | ................ F01K 13/00 122/406.1 |
| 2009/0030254 A1 * | 1/2009 | Spicer | ................ C10G 9/00 585/634 |
| 2017/0113980 A1 | 4/2017 | Radaelli et al. | |

FOREIGN PATENT DOCUMENTS

| | | |
|---|---|---|
| DE | 25 54 666 A1 | 6/1977 |
| DE | 199 01 656 A1 | 7/2000 |
| DE | 10 2006 055973 A1 | 5/2008 |
| DE | 10 2014 018 261 A1 | 6/2016 |
| EP | 0 272 378 A1 | 6/1988 |
| EP | 0 561 220 A1 | 9/1993 |
| EP | 1 939 412 A1 | 7/2008 |
| EP | 2 201 085 B1 | 6/2010 |
| EP | 3 415 587 A1 | 12/2018 |

* cited by examiner

*Primary Examiner* — Randy Boyer
(74) *Attorney, Agent, or Firm* — McGlew and Tuttle, P.C.

(57) ABSTRACT

A quenching system for a plant, operating a cracking furnace, works with liquid as well as gaseous starting materials. The quenching system includes a primary heat exchanger (PQE 10) and a secondary heat exchanger (SQE 11) and a tertiary heat exchanger. A TLX-D exchanger (TLX-D 26) is arranged and configured as the tertiary heat exchanger for dual operation. The TLX-D (26) is connected in series via a TLX-D gas feed line (24) to the SQE 11. The TLX-D (26) is connected to a steam drum (59), which is connected to a feed water line (49), via a TLX-D feed water drain line (34) and a TLX-D riser (46) and a TLX-D downcomer (38). The SQE 11 is connected to the steam drum (59), which is connected to the feed water line (49), via a TLX downcomer (52) and a TLX-riser (57).

12 Claims, 2 Drawing Sheets

QUENCHING SYSTEM

CROSS REFERENCE TO RELATED APPLICATIONS

This application claims the benefit of priority under 35 U.S.C. § 119 of German Application 10 2018 002 086.0, filed Mar. 9, 2018, the entire contents of which are incorporated herein by reference.

TECHNICAL FIELD

The present invention pertains to a quenching system and to a process for a quenching system for operating a cracking furnace with liquid as well as gaseous starting materials, which comprises a primary heat exchanger and a secondary heat exchanger and a tertiary heat exchanger.

BACKGROUND

There are various starting materials that are further processed in a cracking furnace for the operation of an ethylene furnace, which is also referred to as cracking furnace. Among others, such starting materials are, naphtha, also referred to as liquid starting material (liquid feed), or gas, also referred to as gaseous starting material (gas feed) with a high ethylene content. Both starting materials are heated to a high temperature in a cracking furnace and subsequently cooled immediately with a quenching system, which is also designated by QS for short.

A quenching system or QS with a special configuration is needed depending on the starting material because the physical properties of the starting materials are different. Gas as a starting material may be cooled further downwards, for example, from 900° C. to 150° C., than a liquid starting material, which is cooled from about 900° C. to 350° C., because the condensation of gas starts only at markedly lower temperatures.

Consequently, a quenching system for gas feed mode more often than not consists of a primary heat exchanger or referred to as PQE for short and/or a secondary heat exchanger or referred to as SQE for short and a tertiary heat exchanger or also referred to as TQE for short.

A quenching system for liquid feed mode consists only of a PQE and a SQE which are connected in series. A TQE, which is always used as a feed water preheater or boiler feed water preheater, is not installed in such an arrangement, wherein the PQE and SQE are each connected as evaporators and are also operated as such.

DE 10 2014 018 261 A1 is mentioned as state of the art.

In order to be able to operate a quenching system both with liquid as well as with gaseous starting material, a PQE and an SQE and a TQE must be installed. The TQE on the gas side shall be bypassed by means of a bypass in case of a liquid feed mode of operation.

The current mode of operation of a quenching system for gas feed and for liquid feed according to the state of the art is carried out with such a bypass circuit. A gas inlet valve provided in front of a gas inlet pipe of a TQE is open and a bypass valve arranged in the bypass of the TQE is closed in case of a gas feed operation. The gas inlet valve is closed and the bypass valve is open in case of a liquid feed operation.

The drawbacks of the used arrangement of a quenching system for a gas feed and liquid feed mode of operation according to the state of the art are that such an arrangement with bypass control needs a very large space and hence causes high costs, aside from the fact that the technical arrangement and mode of operation cannot sufficiently meet the requirements set for such a quenching system in terms of reliability, ease of performing repairs and ease of maintenance.

SUMMARY

An object of the present invention is to provide a quenching system and a process for a quenching system for operating a cracking furnace with liquid and gaseous starting materials, which improves the high requirements on technical equipment and mode of operation in terms of reliability and costs and guarantees a simple possibility in terms of necessary repairs and maintenance work.

This object of the present invention is accomplished in a generic manner by a Transfer-Line-Exchanger (TLX) for dual or alternate operation or TLX-D for short being arranged and configured as a tertiary heat exchanger, by the TLX-D being connected in series via a TLX-D gas feed line to a secondary heat exchanger or SQE, and by the TLX-D being connected to a steam drum, which is connected to a feed water line, via a TLX-D feed water drain line and a TLX-D riser and a TLX-D downcomer and the SQE being connected to a steam drum, which is connected to a feed water line, via a SQE downcomer and a SQE riser.

Furthermore, the TLX-D is provided with a TLX-D feed water supply line, including a TLX-D feed water supply line valve arranged in it. Further, a TLX-D feed water drain line valve is arranged in the TLX-D feed water drain line and a TLX-D riser valve is arranged in the TLX-D riser and a TLX-D downcomer valve is arranged in the TLX-D downcomer, wherein a cooling of the TLX-D in natural circulation is preferably provided via the TLX-D downcomer and the TLX-D riser.

An essential advantage is also that the TLX-D is connected to the TLX-D feed water supply line provided, including the TLX-D feed water supply line valve installed in it and is connected to the steam drum via the arranged TLX-D feed water drain line, including the TLX-D feed water drain line valve installed in it, wherein a cooling of the TLX-D by forced circulation is provided via the arranged TLX-D feed water supply line and the TLX-D feed water drain line.

The TLX-D is advantageously arranged and configured for a dual operation such that the TLX-D has baffles arranged at a distance, wherein the baffles are arranged in the TLX-D interior enclosed by the TLX-D jacket at right angles to a center line of the horizontally positioned TLX-D, and the arrangement and position of the baffles are predefined based on the additionally resulting generation of steam in the liquid feed mode.

Another advantage is due to the fact that a first baffle is installed in the TLX-D interior of the TLX-D with predefined distance to the TLX-D feed water inlet pipe and the first baffle deflects a feed water flow by 180° on the jacket side and has a free feed water flow cross section, the maximum height of which is in the range of 10% to 40%, preferably 15% to 25% of the TLX-D jacket internal diameter as a function of the predefined process conditions. Further, a second baffle is arranged in the TLX-D interior of the TLX-D with predefined distance to the first baffle, which second baffle deflects feed water by 180° and has a free feed water flow cross section. An additional array of baffles is provided as a function of the length of the TLX-D up to the TLX-D feed water outlet pipe.

Another feature is due to the fact that a corresponding length of a TLX-D with predefined process conditions is predefined on the gas side and the water/steam side, and that a number of arranged baffles is variable as a function of the predefined process conditions, the distance of the respective baffles from one another being in a range of about 100 mm to 800 mm, preferably from 300 mm to 600 mm.

Another advantage is that the baffles have a flattened configuration in the upper area in case of the TLX-D in case of feed water flowing through the horizontally positioned TLX-D at right angles to the TLX-D center line, and that a free volume or a steam space is configured below the TLX-D riser pipes.

An additional advantage is that in case of the TLX-D, the flattening of the baffles is kept so small that, on the one hand, no undesired bypass flow occurs in the gas feed mode during the operation of the TLX-D as a feed water preheater and is configured so large that, on the other hand, the amount of steam generated can be completely discharged in the liquid feed mode during the operation of the TLX-D as an evaporator. It is preferred that the maximum height of the flattening be configured in a range of about 5 mm to 40 mm, and preferably 10 mm to 15 mm.

In a process for a quenching system for operating a cracking furnace with liquid as well as gaseous starting materials, it proved to be especially advantageous that a TLX-D dual heat exchanger or TLX-D is connected as a tertiary heat exchanger for a dual operation, and the TLX-D is operated in the gas feed mode as feed water preheater in case of gaseous starting material and in the liquid feed mode as evaporator in case of liquid starting material, wherein the TLX-D feed water supply line valve and the feed water valve are opened and the TLX-D downcomer valve and the TLX-D riser valve are closed in the gas feed mode.

Another advantage in the process is due to the fact that feed water is guided against the flow direction of the gaseous cracked gas on the jacket side in the counterflow principle and is cooled to a predefined temperature in the TLX-D via the opened TLX-D feed water supply line valve.

Another advantage is achieved by the guided feed water being heated to temperatures from about 150° C. to about 300° C. by means of heat discharged from the cracked gas in the TLX-D.

It also has proven to be advantageous that the TLX-D downcomer valve and the TLX-D riser valve are opened and the TLX-D feed water supply line valve and the feed water valve are closed in the TLX-D in the liquid feed mode, and that feed water is guided to the steam drum via an installed feed water supply line.

Another advantage is that the TLX-D dual heat exchanger is integrated into the saturated steam system or cooling system of the quenching system, wherein water is guided from the steam drum via the TLX-D downcomer and the opened TLX-D downcomer valve until it is distributed to the TLX-D downcomer pipes installed at the TLX-D.

Furthermore, it is advantageous that water flows through the TLX-D from the steam drum on the jacket side up to the TLX-D riser pipes, which are arranged opposite the TLX-D downcomer pipes, wherein cracked gas flowing through the TLX-D is not cooled significantly, not more than 15% cooling of cracked gas inlet temperature, preferably less than 10%.

A special advantage is due to the fact that a cracked gas inlet temperature close to the saturated steam temperature—close to 50°, preferably less than 30° C., above the range of the saturated steam temperature—is reached in the TLX-D due to the special guiding of the water flow, and a small quantity of steam—less than 10 t/h steam, preferably less than 5 t/h—is generated on the water side or the jacket side by the TLX-D jacket, and the steam is carried into the steam drum via the TLX-D riser pipes, via the TLX-D riser, via an opened TLX-D riser valve and the TLX-D steam drum riser pipe.

The TLX-D is advantageously arranged and configured for a dual operation such that the TLX-D can be used both for a mode of operation in the gas feed mode and in the liquid feed mode, and that the TLX-D is provided both as feed water preheater and as evaporator for such a dual operation.

In case of the advantageous arrangement of the TLX-D, the control of the mode of operation takes place via the water/steam circulation and no longer via the gas side of the gas supply from the PQE and SQE.

Further details and advantages of the present invention are explained in detail on the basis of an exemplary embodiment shown in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
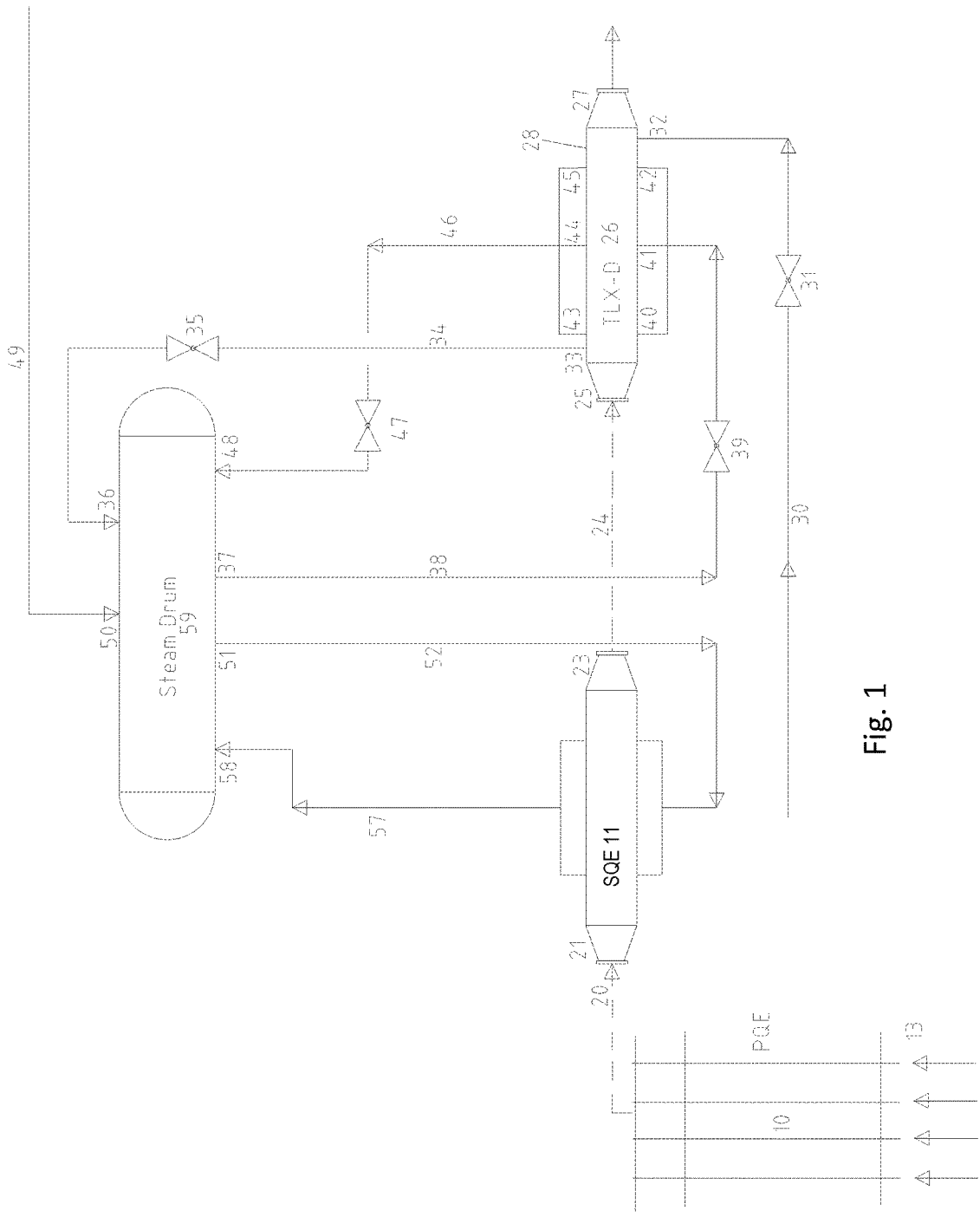
FIG. 1 is a schematic view showing a preferred exemplary embodiment of an arrangement of a cooler system for the mode of operation of a quenching system for gas feed and liquid feed according to the present invention.

A preferred exemplary embodiment of an arrangement of an advantageous quenching system for gas feed mode and liquid feed mode is schematically shown in FIG. 1. A PQE 10 is schematically shown for the sake of greater clarity. Cracked gas is fed from the cracking furnace, not shown, to the PQE 10. in the direction of the arrows 13 indicated. A line 20 coming from the PQE and indicated by an arrow, which guides cracked gas in the direction of the arrow towards a SQE gas inlet pipe 21 of a secondary heat exchanger or SQE 11 for short, is shown The horizontally arranged SQE 11 is connected on the cracked gas side in series with a likewise horizontally arranged TLX-D 26. A cracked gas to be cooled reaches the SQE gas inlet pipe 21 via the line 20 provided and flows through the SQE 11 up to the SQE gas outlet pipe 23. Cracked gas flows through a TLX-D gas inlet pipe 25 up to the TLX-D gas outlet pipe 27 of the TLX-D 26 via an arranged TLX-D gas feed line 24.

The SQE 11 is connected to a steam drum 59 on the cooling side or water/steam side or jacket side via a SQE downcomer 52 and a SQE riser 57. The cooling of the SQE 11 takes place in natural circulation via the SQE downcomer 52 and the SQE riser 57.

The TLX-D 26 is, furthermore, connected to the steam drum 59 via an installed TLX-D downcomer 38, including a TLX-D downcomer valve 39 arranged in it, and via an installed TLX-D riser 46, including a TLX-D riser valve 47 arranged in it. Cooling of the TLX-D 26 takes place in natural circulation via the TLX-D downcomer 38 and the TLX-D riser 46.

Furthermore, the TLX-D 26 is connected to a provided TLX-D feed water supply line 30, including a TLX-D feed water supply line valve 31 installed in it and is connected to the steam drum 59 via a provided TLX-D feed water drain line 34, including a TLX-D feed water drain line valve 35 installed in it. Cooling of the TLX-D 26 takes place by forced circulation via the arranged TLX-D feed water supply line 30 and the TLX-D feed water drain line 34.

The SQE 11 will not be further considered below for the more detailed explanation of the manner of functioning of the TLX-D 26.

The TLX-D 26 may preferably be operated in two different variants. Depending on the cracked gas to be processed, the TLX-D 26 is operated as feed water preheater in the gas feed mode of operation in case of gaseous starting material and as an evaporator in the liquid feed mode of operation in case of liquid starting material. A more detailed explanation of such a different mode of operation was already given in the introduction, so that a further description is dispensed with.

In the gas feed mode of operation of the TLX-D 26, which is then operated as feed water preheater, the TLX-D feed water supply line valve 31 and the TLX-D feed water drain line valve 35 are opened and the TLX-D downcomer valve 39 and the TLX-D riser valve 47 are closed; i.e., the TLX-D downcomer 38 and the TLX-D riser 46 are blocked and no longer in operation.

A feed water supply or boiler feed water supply is carried out by means of a pump, not shown, through the TLX-D feed water supply line 30 via the open TLX-D feed water supply line valve 31 to the TLX-D feed water inlet pipe 32 of the TLX-D 26. Feed water hereby flows through the TLX-D 26 on the jacket side in the counterflow principle, i.e., against the flow direction of the cracked gas, up to the TLX-D feed water outlet pipe 33. Cracked gas, which flows from the TLX-D gas inlet pipe 25 through the TLX-D 26 on the pipe side up to the TLX-D gas outlet pipe 27, is efficiently cooled to a predefined temperature due to the especially effective flow guiding of the feed water through the TLX-D 26 in the counterflow principle. The discharged heat is absorbed by the guided feed water, wherein the feed water is heated to temperatures of about 150° C. up to about 300° C. The heated feed water leaves the TLX-D 26 via the installed TLX-D feed water outlet pipe 33 and is introduced into the steam drum 59 through the arranged TLX-D feed water drain line 34 and via the open TLX-D feed water drain line valve 35 through a TLX-D steam drum feed water pipe 36 installed at the steam drum 59.

In the liquid feed mode of operation of the TLX-D 26, which is then operated as an evaporator, the TLX-downcomer valve 39 and the TLX-D riser valve 47 are opened and the TLX-D feed water supply line valve 31 and the TLX-D feed water drain line valve 35 are closed; i.e., the TLX-D feed water supply line 30 and the TLX-D feed water drain line 34 are blocked and not in operation. A feed water supply to the steam drum 59 takes place via an installed feed water supply line 49 and a feed water pipe 50 arranged at the steam drum. The necessary feed water is fed to the steam drum 59 from an external source in case of the liquid feed mode of operation. Such an external supply of feed water does not have any effect on the mode of operation of the TLX-D 26 and is therefore not considered further.

The TLX-D 26 is integrated into the saturated steam system or cooling system of the quenching system. Water from the steam drum 59 passes through the TLX-D downcomer pipe connection 37, via the TLX-D downcomer 38, via the open TLX-D downcomer valve 39 until it is distributed to the TLX-D downcomer pipes 40, 41, 42, which are installed at the TLX-D 26. Water flows through the TLX-D 26 on the jacket side from the TLX-D downcomer pipes 40, 41, 42 up to the opposite TLX-D riser pipes 43, 44, 45. When flowing through the TLX-D 26, cracked gas, which flows from the TLX-D gas inlet pipe 25 through the TLX-D 26 on the pipe side up to the TLX-D gas outlet pipe 27, is not cooled significantly, not more than 15% cooling of the cracked gas inlet temperature, preferably less than 10%, since the cracked gas inlet temperature is close to the saturated steam temperature of the water, close to 50° C., preferably less than 30° C., above the range of the saturated steam temperature. Hence, only a small quantity of steam, less than 10 t/h steam, preferably less than 5 t/h steam, which is carried into the steam drum 59 through the TLX-D riser pipes 43, 44, 45, via the TLX-D riser 46 and via the open TLX-D riser valve 47 and via the TLX-D steam drum riser pipe 48, is generated on the water side or jacket side of the TLX-D 26. The TLX-D 26 can be operated with very low output due to the preferred configuration. Due to such a mode of operation, a cooling of cracked gas below the condensation temperature is avoided, without a conventional TQE having to be bypassed by means of a bypass.

The advantages in the preferred exemplary embodiment are due to the fact that significant costs can be lowered by a gas-side bypass circuit being able to be avoided and the costly space requirement connected therewith being able to be eliminated.

Significant technical changes in the TLX-D 26 compared to a conventional TQE are configured for a dual operation.

In the exemplary embodiment, the TLX-D feed water inlet pipe 32 and the TLX-D feed water outlet pipe 33 for a TLX-D operated as feed water preheater in the gas feed mode are preferably arranged at the TLX-D 26. Moreover, TLX-D downcomer pipes 40, 41, 42 and TLX-D riser pipes 43, 44, 45 are each preferably installed for a TLX-D 26 operated as evaporator in the liquid feed mode.

The TLX-D feed water inlet pipe 32 and the TLX-D feed water outlet pipe 33 of the horizontally arranged TLX-D 26 are each provided in front of the TLX-D gas outlet pipe 27 and behind the TLX-D gas inlet pipe 25, respectively, on the bottom side and the top side, respectively, at the TLX-D jacket 28. The supply of feed water takes place via the TLX-D feed water inlet pipe 32 installed on the bottom side of the TLX-D jacket 28, and the discharge of the preheated feed water takes place via the TLX-D feed water outlet pipe 33 arranged on the top side of the TLX-D jacket 28.

The number and horizontal position of the TLX-D downcomer pipes 40, 41, 42 and of the TLX-D riser pipes 43, 44, 45 are predefined on the basis of the required generation of steam; i.e., the number of TLX-D riser pipes and TLX-D downcomer pipes shown in FIG. 1 is variable. In this case, a water feed takes place via the TLX-D downcomer pipes 40, 41, 42 installed on the bottom side of the TLX-D jacket 28 and a water/steam discharge takes place via the TLX-D riser pipes 43, 44, 45 of the horizontally positioned TLX-D 26 arranged on the top side of the TLX-D jacket.

An arrangement and position of baffles 62 in the TLX-D interior 29, which is enclosed by the TLX-D jacket 28 of the TLX-D 26, are predefined on the basis of the cracked gas cooling in the gas feed mode. The baffles 62 have a special configuration, which will be shown and described further below. Such an arrangement and position of baffles 62 of the TLX-D 26 are shown in FIG. 2.

Figure 2:
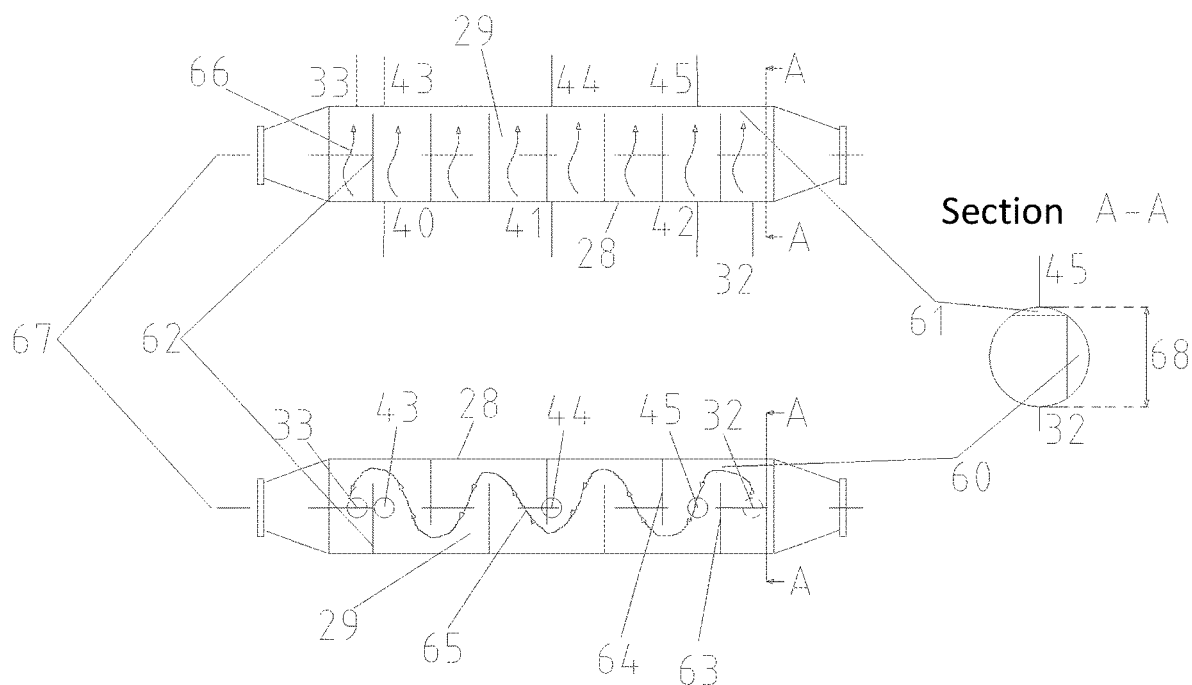
FIG. 2 is a schematic view showing a preferred exemplary embodiment of a configuration of a TQE for the mode of operation of a quenching system for gas feed and liquid feed according to the present invention.

A feed water flow 65 on the jacket side in the gas feed mode indicated by a wavy line is shown in a top view of FIG. 2. Feed water enters the TLX-D 26 through the TLX-D feed water inlet pipe 32 and is deflected by 180° by a first baffle 63 installed in the TLX-D interior 29 of the TLX-D with a predefined distance to the feed water feed pipe and thereby flows through a free feed water flow section 60, the cross section of which is apparent from section A-A, and has a maximum height as a function of predefined process conditions in the range of 10% to 40%, preferably 15% to 25% of the diameter of the TLX-D jacket 28. The feed water is also deflected by 180° and passes through a second free feed water flow section in case of a second baffle 64 arranged in the TLX-D interior 29 of the TLX-D 26 with predefined distance to the first baffle 63.

Such a process is repeated as a function of the length of the TLX-D 26 up to the TLX-D feed water outlet pipe 33. The corresponding length of a TLX-D 26 is predefined on the gas and water/steam sides with predefined precise process conditions. The number of arranged baffles 62 is variable as a function of predefined process conditions. The distance of the respective baffles from one another is in a range of about 100 mm to 600 mm, but preferably from 300 mm to 500 mm.

A water/stream flow 66 on the jacket side in the liquid feed mode indicated by arrows is shown in a lateral view of FIG. 2. The water enters the horizontally positioned TLX-D 26 on the jacket side via the TLX-D downcomer pipes 40, 41, 42 and crosses through the TLX-D at right angles. While the water crosses through the TLX-D 26 at right angles, a partial phase transition of the water takes place. Thus, in addition to water, a steam content is also present. Hence, it can be guaranteed that resulting steam is discharged via the TLX-D riser pipes 43, 44, 45. Therefore, the baffles 62 have a flattened configuration in the upper area. As a result, a free volume or steam space 61, into which resulting steam flows and is discharged via the TLX-D riser pipes 43, 44, 45, forms under the TLX-D riser pipes 43, 44, 45.

When configuring the free volume or steam space 61 or of the flattening of the baffles 62, it can be taken into consideration that the flattening of the baffles is so small that, on the one hand, no undesired bypass flow occurs in the gas feed mode during the operation of the TLX-D 26 as feed water preheater, and so large that, on the other hand, the resulting steam content can be completely discharged in the liquid feed mode during the operation of the TLX-D as evaporator. The maximum height of the cross section of the flattening shall be configured in a range of about 5 mm to 40 mm, and preferably from 10 mm to 15 mm.

A change in the number and position of TLX-D downcomer pipes and TLX-D riser pipes as well as a configured design of baffles are critical for a reliable mode of operation of a TLX-D 26 in the dual operation. Hence, the predefined process conditions are to be taken into consideration in a precise manner when a TLX-D 26 is being configured.

While specific embodiments of the invention have been shown and described in detail to illustrate the application of the principles of the invention, it will be understood that the invention may be embodied otherwise without departing from such principles.

What is claimed is:

1. A quenching system for a plant for operating a cracking furnace with liquid as well as gaseous starting materials, the quenching system comprising:
   a primary heat exchanger, a secondary heat exchanger and a tertiary heat exchanger comprising a transfer-line-exchanger for dual or double or alternate operation in gas mode and liquid feed mode;
   a steam drum;
   a gas feed line;
   a feed water line;
   a transfer-line-exchanger feed water drain line;
   a transfer-line-exchanger riser;
   a transfer-line-exchanger downcomer;
   a secondary heat exchanger downcomer, wherein:
   the transfer-line-exchanger is connected in series via the gas feed line to the secondary heat exchanger;
   the steam drum is connected to the feed water line;
   the transfer-line-exchanger is connected to the steam drum via the transfer-line-exchanger feed water drain line and the transfer-line-exchanger riser and the transfer-line-exchanger downcomer;
   the secondary heat exchanger is connected to the steam drum via the secondary heat exchanger downcomer and by the secondary heat exchanger riser.

2. A quenching system in accordance with patent claim 1, further comprising a transfer-line-exchanger feed water supply line with a transfer-line-exchanger feed water supply line valve, wherein:
   a transfer-line-exchanger feed water drain line valve is arranged in the transfer-line-exchanger feed water drain line;
   a transfer-line-exchanger downcomer valve is arranged in the transfer-line-exchanger downcomer;
   a transfer-line-exchanger riser valve is arranged in the transfer-line-exchanger riser; and
   a cooling of the transfer-line-exchanger with natural circulation is provided via the transfer-line-exchanger downcomer and the transfer-line-exchanger riser.

3. A quenching system in accordance with patent claim 1, further comprising a transfer-line-exchanger feed water supply line with a transfer-line-exchanger feed water supply line valve wherein:
   the transfer-line-exchanger is connected to the transfer-line-exchanger feed water supply line;
   a transfer-line-exchanger feed water drain line valve is arranged in the transfer-line-exchanger feed water drain line connecting the steam drum to the transfer-line-exchanger; and
   a cooling of the transfer-line-exchanger by forced circulation is provided via the transfer-line-exchanger feed water supply line and the transfer-line-exchanger feed water drain line.

4. A quenching system in accordance with patent claim 1, wherein:
   the transfer-line-exchanger is positioned extending horizontally;
   the transfer-line-exchanger comprises baffles arranged at a distance from one another;
   the baffles are arranged and positioned, in a transfer-line-exchanger interior enclosed by a transfer-line-exchanger jacket, at right angles to a transfer-line-exchanger center line of the horizontally extending transfer-line-exchanger;
   the arrangement and position of the baffles are predefined based on a generation of steam additionally resulting in a liquid feed mode.

5. A quenching system in accordance with patent claim 4, wherein:
   a first baffle of the baffles of the transfer-line-exchanger is positioned and arranged at a predefined distance to the transfer-line-exchanger feed water inlet pipe;

the first baffle deflects a feed water flow by 180° on a jacket side and has a free feed water flow cross section;
a maximum height of the free feed water flow cross section of the first baffle is in a range of 10% to 40% of a transfer-line-exchanger jacket internal diameter as a function of the predefined process conditions;
a second baffle of the baffles of the transfer-line-exchanger is positioned and arranged at a predefined distance to the first baffle;
the second baffle deflects feed water by 180° and has second baffle a free feed water flow cross section;
an additional array of baffles of the baffles of the transfer-line-exchanger is provided as a function of a length of the transfer-line-exchanger up to a transfer-line-exchanger feed water outlet pipe.

6. A quenching system in accordance with patent claim 5, wherein:
the length of the transfer-line-exchanger with predefined process conditions is predefined on a gas side and a water/steam side;
a number of the baffles is variable as a function of the predefined process conditions; and
the distance of the respective baffles from one another is in a range of about 100 mm to 800 mm.

7. A quenching system in accordance with patent claim 4, wherein:
a first baffle of the baffles of the transfer-line-exchanger is positioned and arranged at a predefined distance to the transfer-line-exchanger feed water inlet pipe;
the first baffle deflects a feed water flow by 180° on a jacket side and has a free feed water flow cross section;
a maximum height of the free feed water flow cross section of the first baffle is in a range of 15% to 25% of a transfer-line-exchanger jacket internal diameter as a function of the predefined process conditions;
a second baffle of the baffles of the transfer-line-exchanger is positioned and arranged at a predefined distance to the first baffle;
the second baffle deflects feed water by 180° and has second baffle a free feed water flow cross section;
an additional array of baffles of the baffles of the transfer-line-exchanger is provided as a function of a length of the transfer-line-exchanger up to a transfer-line-exchanger feed water outlet pipe.

8. A quenching system in accordance with patent claim 5, wherein:
the length of the transfer-line-exchanger with predefined process conditions is predefined on a gas side and a water/steam side;
a number of the baffles is variable as a function of the predefined process conditions; and
the distance of the respective baffles from one another is in a range of about 300 mm to 600 mm.

9. A quenching system in accordance with patent claim 4, wherein:
the baffles are arranged in the transfer-line-exchanger at right angles to the transfer-line-exchanger center line in a case of feed water flowing through the horizontally positioned transfer-line-exchanger;
the baffles have a flattened configuration in an upper area;
the transfer-line-exchanger has transfer-line-exchanger riser pipes; and
a free volume or a steam space of the transfer-line-exchanger is configured to be below the transfer-line-exchanger riser pipes.

10. A quenching system in accordance with patent claim 9, wherein:
the flattened configuration of the baffles is small enough such that no undesired bypass flow occurs in a gas feed mode during an operation of the transfer-line-exchanger as a feed water preheater; and
the flattened configuration of the baffles large enough such that an amount of steam generated is completely discharged in the liquid feed mode during an operation of the transfer-line-exchanger as an evaporator; and
a the maximum height of the flattening is configured in a range of about 5 mm to 40 mm.

11. A quenching system for a plant for operating a cracking furnace with liquid as well as gaseous starting materials, the quenching system comprising:
a primary heat exchanger;
a secondary heat exchanger;
a steam drum;
a gas feed line;
a feed water line;
a transfer-line-exchanger feed water line with a transfer-line-exchanger feed water line valve;
a transfer-line-exchanger feed water drain line with a transfer-line-exchanger feed water drain line valve;
a transfer-line-exchanger riser with a transfer-line-exchanger riser valve;
a transfer-line-exchanger downcomer with a transfer-line-exchanger downcomer valve;
a secondary heat exchanger downcomer; and
a transfer-line-exchanger arranged and configured as a tertiary heat exchanger for a dual or double or alternate operation in gas feed mode and liquid feed mode, wherein:
the transfer-line-exchanger is connected in series via the gas feed line to the secondary heat exchanger;
the steam drum is connected to the feed water line;
the transfer-line-exchanger is connected to the steam drum via the transfer-line-exchanger feed water drain line and the transfer-line-exchanger riser and the transfer-line-exchanger downcomer;
the secondary heat exchanger is connected to the steam drum via the secondary heat exchanger downcomer and by the secondary heat exchanger riser;
the transfer-line-exchanger feed water supply line valve of a transfer-line-exchanger feed water supply line and the feed water drain valve of the transfer-line-exchanger feed water drain line are opened to provide a liquid feed mode; and
the transfer-line-exchanger downcomer valve of the transfer-line-exchanger downcomer and the transfer-line-exchanger riser valve of the transfer-line-exchanger riser are closed to provide a gas feed mode.

12. A quenching system in accordance with patent claim 11, further comprising another heat exchanger operatively connected between the secondary heat exchanger and the transfer-line-exchanger arranged and configured as the tertiary heat exchanger for dual operation.

* * * * *